(12) United States Patent
Sun et al.

(10) Patent No.: US 8,460,547 B2
(45) Date of Patent: Jun. 11, 2013

(54) HOLLOW POROUS MICROSPHERES

(75) Inventors: Delai Darren Sun, Singapore (SG); Pei Fung Lee, Singapore (SG); Xiwang Zhang, Singapore (SG); Jianhong Du, Singapore (SG); James O. Leckie, Stanford, CA (US)

(73) Assignees: Nanyang Technological University, Singapore (SG); The Board of Trustees of the Leland Stanford Junior University, Palo Alto, CA (US)

( * ) Notice: Subject to any disclaimer, the term of this patent is extended or adjusted under 35 U.S.C. 154(b) by 578 days.

(21) Appl. No.: 12/669,427

(22) PCT Filed: Jul. 14, 2008

(86) PCT No.: PCT/SG2008/000250
§ 371 (c)(1),
(2), (4) Date: Jun. 28, 2010

(87) PCT Pub. No.: WO2009/011658
PCT Pub. Date: Jan. 22, 2009

(65) Prior Publication Data
US 2010/0264097 A1     Oct. 21, 2010

Related U.S. Application Data

(60) Provisional application No. 60/950,558, filed on Jul. 18, 2007.

(51) Int. Cl.
*C02F 3/00*     (2006.01)

(52) U.S. Cl.
USPC ........... 210/615; 210/616; 210/617; 210/263; 210/505

(58) Field of Classification Search
USPC ................... 210/615–617, 263, 505
See application file for complete search history.

(56) References Cited

U.S. PATENT DOCUMENTS

| | | | |
|---|---|---|---|
| 4,867,931 A | 9/1989 | Cochran, Jr. | 264/9 |
| 4,937,210 A | 6/1990 | Jones et al. | 501/80 |
| 5,512,094 A | 4/1996 | Linton | 106/409 |
| 7,485,224 B2 * | 2/2009 | Jones et al. | 210/241 |

FOREIGN PATENT DOCUMENTS

JP     10 028875     2/1998

OTHER PUBLICATIONS

Bender et al., "Spectroscopic investigation of the composition of electrospun titania nanofibers" Surface and Interface Analysis 38: 1252-1256, 2006.
Cao et al., "Sol-Gel Template Synthesis of an Array of Single Crystal CdS Nanowires on a Porous Alumina Template" Adv. Mater. 13(18): 1393-1394, Sep. 14, 2001.
Chen et al., "Synthesis of Titanium Dioxide ($TiO_2$) Nanomaterials" Journal of Nanoscience and Nanotechnology 6(4): 906-925, 2006.
Chen et al., "Titanium Dioxide Nanomaterials: Synthesis, Properties, Modifications, and Applications" Chem. Rev. 107: 2891-2959, 2007.

(Continued)

*Primary Examiner* — Chester Barry
(74) *Attorney, Agent, or Firm* — Seed IP Law Group PLLC

(57) ABSTRACT

The present invention refers to a hollow microsphere having a porous circumferential wall comprised of nanofilaments.

19 Claims, 9 Drawing Sheets

Initial Suspension droplets   Shrinking suspension droplets   Products

OTHER PUBLICATIONS

Cheng et al., "Fabrication and characterization of nanotubular semiconductor oxides $In_2O_3$ and $Ga_2O_3$" J. Mater. Chem. 11: 2901-2901, 2001.

Dong et al., "Multifunctional, Catalytic Nanowire Membranes and the Membrane-Based 3D Devices" Journal of Physical Chemistry B Letters 110: 16819-16822, 2006.

Du et al., "Potassium titanate nanowires: Structure, growth, and optical properties" Physical Review B: 67: 035323-1-035323-7, 2003.

Endo et al., "Buckypaper from coaxial nanotubes" Nature 433: 476, Feb. 3, 2005.

Fang et al., "Removal of humic acid foulant from ultrafiltration membrane surface using photocatalytic oxidation process" Water Science & Technology 51(6-7): 373-380, 2005.

Fujishima et al., "Titanium dioxide photocatalysis" Journal of Photochemistry and Photobiology C: Photochemistry Reviews 1: 1-21, 2000.

Gu et al., "$V_2O_5$ nanofibre sheet actuators" Nature Materials 2: 316-319, May 2003.

Hidalgo et al., "Hydrothermal preparation of highly photoactive $TiO_2$ nanoparticles" Catalysis Today 129: 50-58, 2007.

Hoffmann et al., "Environmental Applications of Semiconductor Photocatalysis" Chem. Rev. 95: 69-96, 1995.

Houas et al., "Photocatalytic degradation pathway of methylene blue in water" Applied Catalysis B: Environmental 31: 145-157, 2001.

Imhof et al., "Ordered macroporous materials by emulsion templating" Nature 389: 948-951, Oct. 30, 1997.

Kasuga et al., "Formation of Titanium Oxide Nanotube" Langmuir 14: 3160-3163, 1998.

Kolen'ko et al., "Photocatalytic properties of titania powders prepared by hydrothermal method" Applied Catalysis B: Environmental 54: 51-58, 2004.

Kresge et al., "Ordered mesoporous molecular sieves synthesized by a liquid-crystal template mechanism" Nature 359: 710-712, Oct. 22, 1992.

Lakshmi et al., "Sol-Gel Template Synthesis of Semiconductor Oxide Micro- and Nanostructures" Chem. Mater. 9: 2544-2550, 1997.

Li et al., "Photocatalytic Oxidation Using a New Catalyst—$TiO_2$ Microsphere—for Water and Wastewater Treatment" Environ. Sci. Technol. 37: 3989-3994, 2003.

Li et al., "Electrospinning of Nanofibers: Reinventing the Wheel?" Adv. Mater. 16(14): 1151-1170, Jul. 19, 2004.

Liu et al., "One-Step Fabrication and High Photocatalytic Activity of Porous $TiO_2$ Hollow Aggregates by Using a Low-Temperature Hydrothermal Method Without Templates" Chem. Eur. J. 13: 1851-1855, 2007.

Liu et al., "An Efficient Bicomponent $TiO_2/SnO_2$ Nanofiber Photocatalyst Fabricated by Electrospinning with a Side-by-Side Dual Spinneret Method" Nano Letters 7(4): 1081-1085, 2007.

Lorenc-Grabowska et al., "Adsorption of lignite-derived humic acids on coal-based mesoporous activated carbons" Journal of Colloid and Inferface Science 284: 416-423, 2005.

Madhugiri et al., "Electrospun mesoporous titanium dioxide fibers" Microporous and Mesoporous Materials 69: 77-83, 2004.

Mao et al., "Environmentally Friendly Methodologies of Nanostructure Synthesis" Small 3(7): 1122-1139, 2007.

McCann et al., "Electrospinning of nanofibers with core-sheath, hollow, or porous structures" J. Mater. Chem. 15: 735-738, 2005.

Miao et al., "Electrochemically Induced Sol-Gel Preparation of Single-Crystalline $TiO_2$ Nanowires" Nano Letters 2(7): 717-720, 2002.

Musin et al., "Quantum size effect in core-shell structured silicon-germanium nanowires" Physical Review B 74: 165308-1-165308-5, 2006.

Nagaoka et al., "Preparation of carbon/$TiO_2$ microsphere composites from cellulose/$TiO_2$ microsphere composites and their evaluation" Journal of Molecular Catalysis A: Chemical 177: 255-263, 2002.

Paulraj et al., "Characterisation of $In_2S_3$ and ZnO thin films for photovoltaic application using Photothermal deflection technique" J. Phys. IV France 125: 469-472, 2005.

Pavasupree et al., "Synthesis of titanate, $TiO_2$ (B), and anatase $TiO_2$ nanofibers from natural rutile sand" Journal of Solid State Chemistry 178: 3110-3116, 2005.

Qiao et al., "Photocatalytic oxidation technology for humic acid removal using a nano-structured $TiO_2/Fe_2O_3$ catalyst" Water Science and Technology 47(1): 211-217, 2002.

Sigmund et al., "Processing and Structure Relationships in Electrospinning of Ceramic Fiber Systems" J. Am. Ceram. Soc. 89(2): 395-407, 2006.

Sivalingam et al., "Photocatalytic degradation of various dyes by combustion synthesized nano anatase $TiO_2$," Applied Catalysis B: Environmental 45: 23-38, 2003.

Subbiah et al., "Electrospinning of Nanofibers" Journal of Applied Polymer Science 96: 557-569, 2005.

Van Schalkwyk et al., "Application of a $WO_3/SiO_2$ catalyst in an industrial environment: part I" Applied Catalysis A: General 255: 121-131, 2003.

Wang et al., "Photocatalytic Activity of a Hierarchically Macro/Mesoporous Titania" Langmuir 21: 2552-2559, 2005.

Wang et al., "Fabrication and Characterization of Polycrystalline $WO_3$ Nanofibers and Their Application for Ammonia Sensing" J. Phys. Chem B 110: 23777-23782, 2006.

Wu et al., "Transparent, Conductive Carbon Nanotube Films" Science 305: 1273-1276, 2004.

Yoshida et al., "Syntheses of $TiO_2$(B) nanowires and $TiO_2$ anatase nanowires by hydrothermal and post-heat treatments" Journal of Solid State Chemistry 178: 2179-2185, 2005.

Yu et al., "Preparation of highly photocatalytic active nano-sized $TiO_2$ particles *via* ultrasonic irradiation" Chem. Commun. 1942-1943, 2001.

Yuan et al., "Titanium oxide nanotubes, nanofibers and nanowires" Colloids and Surfaces A: Physicochem. Eng. Aspects 241: 173-183, 2004.

Zhang et al., "Preparation and characterization of nanocrystal grain $TiO_2$ porous microspheres" Applied Catalysis B: Environmental 40: 253-258, 2003.

Zhang et al., "Starch Gel Templating of Spongelike Macroporous Silicalite Monoliths and Mesoporous Films" Chem. Mater. 14: 1369-1375, 2002.

Zhang et al., "Microwave assisted photocatalytic degradation of high concentration azo dye Reactive Brilliant Red X-3B with microwave electrodeless lamp as light source" Dyes and Pigments 74: 536-544, 2007.

Zhang et al., "Effect of operating parameters on microwave assisted photocatalytic degradation of azo dye X-3B with grain $TiO_2$ catalyst" Journal of Molecular Catalysis A: Chemical 237: 199-205, 2005.

Zhang et al., "Strong, Transparent, Multifunctional, Carbon Nanotube Sheets" Science 309: 1215-1219, 2005.

Zhang et al., "Electrochemical Lithium Storage of Titanate and Titania Nanotubes and Nanorods" J. Phys. Chem. C 111: 6143-6148, 2007.

\* cited by examiner nanowire or nanobelt nanofiber nanotube woven    non-woven

Initial Suspension droplets    Shrinking suspension droplets    Products

HOLLOW POROUS MICROSPHERES

CROSS-REFERENCE TO RELATED APPLICATIONS

This application claims the benefit of priority of U.S. provisional application No. 60/950,558, filed 18 Jul. 2007, the contents of it being hereby incorporated by reference in its entirety for all purposes.

FIELD OF THE INVENTION

The present invention refers to a hollow microsphere having a porous circumferential wall comprised of nanofilaments.

BACKGROUND TO THE INVENTION

Meso- and macroporous compositions of different materials have found great utility as catalysts and sorption media because of their large internal surface area (Kresge, C. T., Leonowicz, M. E., et al., 1992, Nature, vol. 359, p. 710).

For example macroporous materials with pore diameters comparable to optical wavelengths are predicted to have unique and highly useful optical properties such as photonic bandgaps and optical stop-bands. Control over the pore size distribution can lead to improved macroporous materials for applications as catalytic surfaces and supports, adsorbents, chromatographic materials, filters, light-weight structural materials, and thermal acoustic and electrical insulators (Imhof, A., Pine, D. J., 1997, Nature, vol. 389, p. 948).

Do to their versatile applicability a high demand exists for further porous materials having some or all of the above described features.

SUMMARY OF THE INVENTION

The present invention refers to a hollow microsphere having a porous circumferential wall comprised of nanofilaments. In one aspect the diameter of such hollow microspheres is between about 1 to 200 µm. The nanofilaments are made of a material which includes, but is not limited to a metal oxide, metal sulfide, carbon, polymer or mixtures thereof.

In another aspect the present invention refers to a method of manufacturing at least one hollow microsphere according to the present invention, wherein the method comprises spray drying of a mixture of a surfactant and nanofilaments. The nanofilaments are made of a material which includes, but is not limited to a metal oxide, metal sulfide, carbon, polymer or mixtures thereof.

In still another aspect the present invention refers to a method of cleaning contaminated water comprising mixing the contaminated water with the hollow microspheres of the present invention or hollow microspheres obtained by the method of the present invention, wherein the hollow microspheres are made of a photocatalytic material.

In still another aspect the present invention refers to the use of a hollow microsphere of the present invention or obtained by a method of the present invention as catalyst, or chromatographic material, or light-weight structural material, or thermal insulators, or acoustic insulators or electrical insulators. The catalysts can be used for cleaning contaminated water or for hydrogen production or for cracking oil or for energy production or for the manufacture of solar cells.

BRIEF DESCRIPTION OF THE DRAWINGS

The invention will be better understood with reference to the detailed description when considered in conjunction with the non-limiting examples and the accompanying drawings, in which:

FIG. 1A(a) and (c) scale bar: 10 µm; FIG. 1A(b) and (d) scale bar: 1 µm. FIG. 1A(b) and (d) show the porous structure of the hollow microsphere as well as the non-woven alignment of the nanofilaments, in this case $TiO_2$ nanowires, which form the circumferential wall of the hollow microsphere of the present invention.

FIG. 1C illustrates graphically the difference in structure between nanofibers and nanowires (also nanobelt). While the nanofiber has a round cross section the nanowire or nanobelt has a rectangular cross section. Nanotubes have either a round or a rectangular cross section but are hollow inside (hollow section is indicated in FIG. 1C by the bright area in the center of the nanotubes).

In FIG. 6 the x-axis shows the temperature. The left y-axis shows the absolute weight change (weight (%)) while the right y-axis shows the change of weight of the hollow microspheres per minute (derivative weight % (%/min)). In this experiment it has been analyzed how the surfactants are removed from the hollow microspheres formed during spray drying. FIG. 6 shows that the surfactants have been mainly removed at two critical temperatures, namely, 140° C. and 330° C. At 350° C., all surfactant has almost been removed from the hollow microspheres.

FIG. 7(a) and (b)2 g/L, (c) and (d) 4 g/L, (e) and (f) 6 g/L, (g) and (h) 10 g/L nanofilaments. FIG. 7(a) shows the image of the products of 2 g/L nanowire suspension. FIG. 7(a) shows that the number of assembled microspheres is still small. It is hypothesized that the nanowire concentration should be higher for manufacture of more microspheres. As the nanowire concentration increased to 4 g/L, large amounts of microspheres become visible in the products as shown in FIG. 7c. High magnification image (FIG. 7(d)) clearly shows the porous microspheres are hollow and with a larger opening on the shell. The shell which consists of nanowires, has a porous morphology. At a nanowire concentration of 6 g/L, there has been a further increase in the quantities of microspheres in the products. However, the one central opening has been absent from the shell as shown in FIG. 7(e). High magnification image (FIG. 7(f)) shows however that the porous morphology of the microsphere shell remained intact. Through the net pores between nanowires, the hollow structure is also visible. At a nanowire concentration of 8 g/L, the microspheres became close-grained as shown in FIG. 1A(a) and (b). The pore size of the microspheres became smaller. Further increase in the concentration of nanowires to 10 g/L resulted in formation of more close-grained microspheres as shown in FIG. 7(g) and (h). Scale bar FIG. 7, FESEM images on the left side: 10 μm; FESEM images on the right side: 1 μm.

FIG. 8(a) nanofilament suspension droplet without surfactant, (b) nanofilament suspension droplet with low nanofilament concentration, (c) nanofilament suspension droplet with medium nanofilament concentration and (d) nanofilament suspension droplet with high nanofilament concentration. FIG. 8 shows that by increasing the concentration of nanofilaments the pore size can be controlled as a higher nanofilaments concentration leads to a denser circumferential wall of the hollow porous microsphere.

FIG. 9(a) shows MB removal vs. time and Figure (b) shows the absolute TOC removal after 90 min. MB reduction in photolysis was less than 30% after an irradiation time of 90 min. The photocatalytic degradation of MB in $TiO_2$ nanowire hollow microspheres and P25 suspensions fitted the pseudo-first-order model. The apparent rate constants for the three kinds of nanowire microspheres NM4 (4 g/L nanofilament suspension), NM6 (6 g/L nanofilament suspension) and NM8 (8 g/L nanofilament suspension) were 0.0639, 0.0632 and 0.0621 $min^{-1}$, respectively. These were better than that for P25 (0.0556 $min^{-1}$). In water, P25 $TiO_2$ nanoparticles coagulate easily to form submicron aggregates due to their high surface energy, and this results in the reduction of contact area with UV and organic reactants. The total organic content (TOC) results also showed similar results as shown in FIG. 9(b).

FIG. 10(a) shows MB removal and (b) shows TOC removal. It can be concluded that the structure of the hollow microspheres of the present invention are stable even when reused several times.

DETAILED DESCRIPTION OF THE INVENTION

Figure 1A:
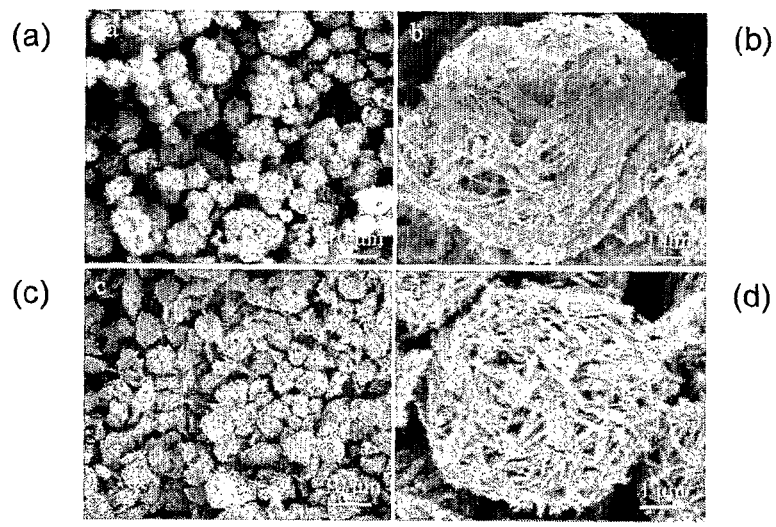
FIG. 1A shows FESEM images of (a), (b) hollow $TiO_2$ microspheres as-synthesized and (c), (d) calcined nanowire $TiO_2$ microspheres at 600° C. $TiO_2$ nanowire and F127 surfactant concentration in suspension feed for spray drying have been: 8 g/L and 0.1 wt %.

The present invention refers to a hollow microsphere having a porous circumferential wall comprised or consisting of nanofilaments. The microspheres can have a diameter between about 1 to about 200 μm. In other words hollow microspheres are described having a circumferential porous wall, i.e. the wall or outer wall which confines the hollow space or void inside the microsphere, wherein the wall is made of nanofilaments. The term "nanofilament" refers to nanofibers, nanotubes and nanowires. A nanofiber is in general characterized by a round cross section as illustrated in FIG. 1C while a nanowire, also called nanobelt, is characterized by a rectangular cross section as illustrated in FIG. 1C. Nanotubes are nanofibers or nanowires which have a hollow core as illustrated in FIG. 1C. The microspheres of the present invention can be made either of nanofibers, nanowires, nanotubes or mixtures of both.

Figure 1B:
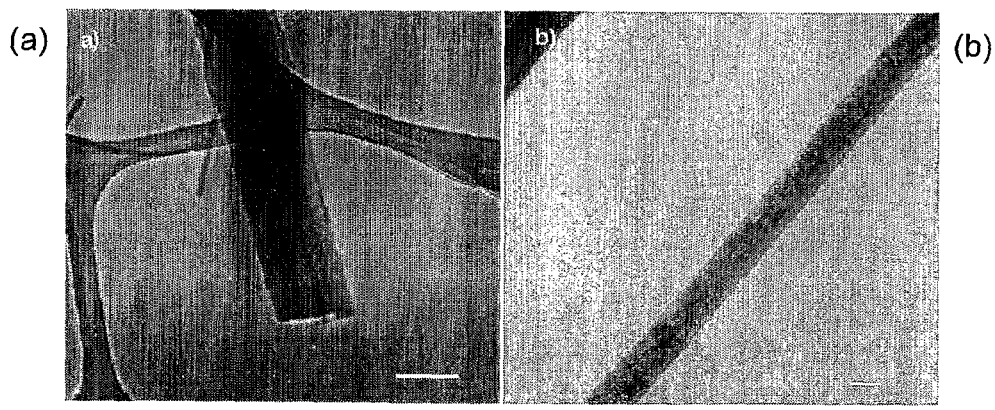
FIG. 1B(a) and (b) show TEM images of $TiO_2$ nanowires of a hollow microsphere of the present invention. The scale bars for FIG. 1B(a) and (b) are 100 nm and 20 nm, respectively.
Figure 1C:
FIG. 1C shows a cross sectional view of nanofilaments.
Figure 1C:
Figure 1C:
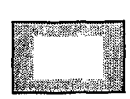

Nanofilaments as illustrated in FIG. 1B are further characterized by their high length to diameter aspect ratio. In the present case nanofilaments can be several (1 to 5 or 10) micrometers long while their largest diameter is only between about 10 to 500 nm or about 10 to 200 nm. In one example their largest diameter is about 20 to 100 nm.

The structure of the hollow microspheres whose circumferential wall is made of nanofilaments is a result of its unique way of manufacturing which will be described further below. Other hollow porous microspheres known in the art whose outer wall is not made of nanofilaments have been described earlier, for example, by Nagaoka, S., Hamasaki, Y. et al. (2002, J Mol Catalysis A: Chemical, vol. 177, p. 255), Li, X.

Z. and Liu, H. (2003, Environ. Sci. Technol., vol. 37, p. 3989) and Liu, Z., Sun, D. D. et al. (2007, Chem. Eur. J., vol. 13, p. 1851 (e-pub. 29 Nov. 2006)).

Figure 1D:
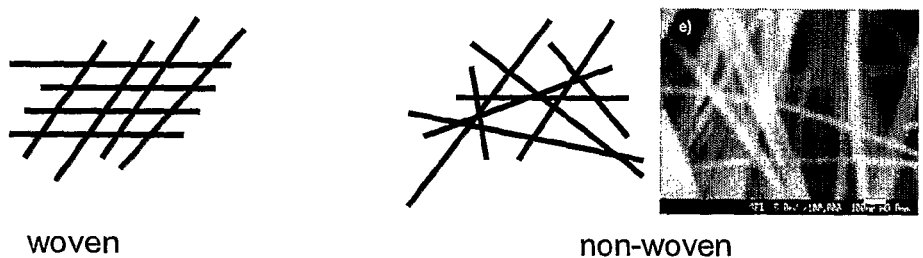
FIG. 1D is a graphical illustration showing the difference between a woven and non-woven (random) structure of the nanofilaments in the circumferential wall of the hollow microspheres. It can be seen that in a woven structure the orientation of each nanofilament with respect to all other nanofilaments is more defined than in the non-woven structure. As can also be seen, woven structure means not that a perfect parallel orientation and distance of the nanofilaments to each other exists but an orientation which is much closer to a well defined and regular orientation of the nanofilaments as in the non-woven structure. Scale bar (white bar) small picture on the right side: 100 nm.
Figure 8:
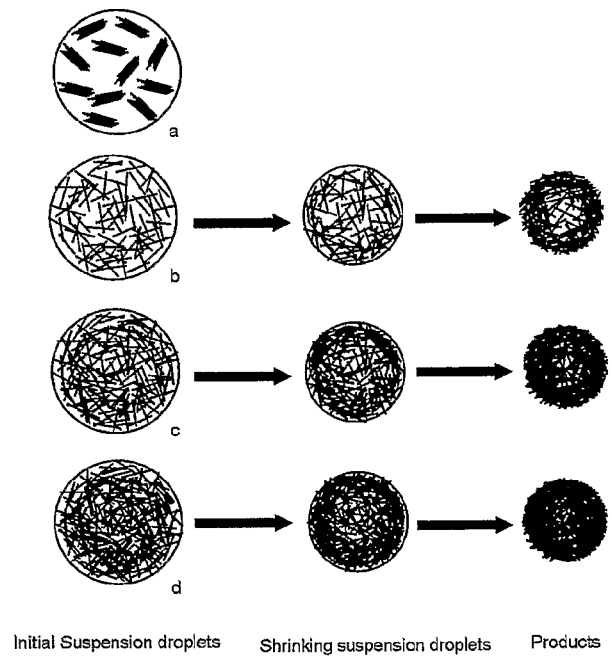
FIG. 8 illustrates a mechanism model of the formation of hollow microspheres via surfactant-mediated spray-drying process. The "initial suspension droplets" illustrate the suspension as it is dispensed through the nozzle in the evaporation tube of the spray dryer. The "shrinking suspension droplet" illustrates an intermediate state of the microsphere during evaporation of the solvent in the evaporation tube of the spray dryer and the "product" shows the final porous hollow microsphere exiting the spray dryer through the cyclone.

As can be seen from the close-up view of the hollow microspheres, for example, in FIG. 1A(b), (d) and the schematic illustration in FIG. 8 the nanofilaments forming the circumferential wall of the hollow microspheres are oriented or aligned in a non-woven, i.e. random, structure. The difference between a non-woven or random structure compared to a woven or regular structure is illustrated in FIG. 1D. This random alignment of the nanofilaments results in the pores of the microsphere having different sizes. Thus, the pores in the circumferential wall of the hollow microspheres are formed between the randomly aligned nanofilaments.

The pores in the circumferential wall of the hollow microsphere include macropores, mesopores and mixtures thereof. According to the definition of the International Union of Pure and Applied Chemistry (IUPAC) the term "mesopore/mesoporous" refers to pore size in the range of 2 to 50 nm and this range enhances the adsorption of contaminants (Lorenc-Grabowska, E. and Gryglewicz, G., 2005, Journal of Colloid and Interface Science, vol. 284, p. 416-423). According to IUPAC, a pore size below 2 nm is termed a micropore range and >50 nm is termed macropore range. In one example of the present invention macropores have a size between 50 nm to about 200 nm. In another example the average pore size is about 100 nm and thus lies in the macroporous range.

The size of the hollow microspheres depends mainly on the method of its manufacture and can therefore be varied over a broad range depending on the desired application as will be explained in more detail further below. As mentioned above, the hollow microspheres of the present invention can have a diameter (or size) between about 1 μm and about 200 μm or 100 μm or 50 μm. Depending on the spray dryer which is used for its manufacture the diameter can be even larger. In another example the hollow microspheres can have a diameter between about 2 to 10 μm or 3 to 8 μm. As the shape of the "microsphere" is most of the time not perfectly round it should be noted that when referring to the "diameter" it is meant the largest straight distance from one end to another of a "pore".

Due to their porous circumferential wall and due to the fact that they are hollow the microspheres of the present invention have a high surface area. The surface area for the hollow microspheres of the present invention has been determined using the BET method which is named according to their inventors Brunauer, Emmett, and Teller. For example, hollow microspheres having a diameter of about 3-10 μm and a pore size between about 50-150 nm have a BET surface of 38.2 $m^2/g$.

The nanofilaments which are used to manufacture the hollow microspheres of the present invention can be made of any material as long as those materials can be formed into nanofilaments. The nanofilaments used herein can be made of a metal oxide, metal sulfide, carbon, polymer or mixtures thereof. Hollow microspheres of the present invention made of such nanofilaments find multiple applications.

Hollow microspheres with nanofilaments of carbon can be used, for example, in composites and syntactic foam for a variety of applications. Due to their good mobility and thin walls, which permit deformation in response to sound pressure, such microspheres can be used in the production of carbon microphones. Also, specially processed pitch carbon microsphere composites are suitable for use as honeycomb fillers for high-temperature or ionizing radiation fields.

Polymers which are suitable as material for nanofilaments include, but are not limited to 1,1,1,3,3,3-hexafluoroisopropanol (HFIP), poly(urethanes), poly(siloxanes), poly(silicones), poly(ethylene), poly(vinyl pyrrolidone), polyaniline/polyethylene oxide blends, poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO) and polyorthoesters. It is also possible to use blends of different polymers listed above.

Other polymers which can be used include, but are not limited to collagen, poly(alpha esters), such as poly(lactate acid), poly(glycolic acid), polyorthoesters, polyanhydrides and their copolymers. Further examples of polymers which can be used include cellulose ether, cellulose acetate, cellulose, cellulose ester, chitosan, gelatin, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. Depending on their application the material may be impregnated with suitable antimicrobial agents.

For example, the nanofilaments can also be made of at least one semiconductor. Examples for semiconductors include, but are not limited to $SiO_2$, $TiO_2$, $ZnO$, $Fe_2O_3$, $W_2O_3$, $SrTiO_3$, CdS and ZnS. These semiconductors can act as sensitizers for light-reduced redox processes due to their electronic structure, which is characterized by a filled valence band and an empty conduction band. When a photon with an energy of hv matches or exceeds the bandgap energy, $E_g$ of the semiconductor, an electron, $e_{cb}^-$, is promoted from the valence band, VB, into the conduction band, CB, leaving a hole, $h_{vb}^+$ behind. Excited state conduction-band electrons and valence-band holes can recombine and dissipate the input energy as heat, get trapped in metastable surface states, or react with electron donors and electron acceptors adsorbed on the semiconductor surface or within the surrounding electrical double layer of the charged particles.

Thus, these semiconductors can serve for the remediation of contaminants, such as alkanes, aliphatic alcohols, aliphatic carboxylic acids, alkenes, phenols, aromatic carboxylic acids, dyes, PCB's, simple aromatics, halogenated alkanes and alkenes, surfactants, and pesticides as well as for the reductive deposition of heavy metals (e.g., $Pt^{4+}$, $Au^{3+}$, $Rh^{3+}$, Cr(VI)) from aqueous solution to surfaces. In many cases, complete mineralization of organic compounds has been reported when using these semiconductors.

Metal sulfides include, but are not limited to CdS, $In_2S_3$ and ZnS. ZnS for example emits light on excitation by x-rays or electron beam, making hollow microspheres with nanofilaments of ZnS useful for, e.g., x-ray screens and cathode ray tubes. Hollow microspheres with nanofilaments of CdS can be used, for example, as components in photoresistors and solar cells. Hollow microspheres with nanofilaments of ZnO and $In_2S_3$ are used as thin films for photovoltaic applications (Paulraj, M., Ramkumar, S., et al., 2005, Journal de Physique IV, vol. 125, no. 1, p. 469). Therefore, such porous hollow microspheres can be used for the manufacture of solar cells and/or photoresistors.

In other applications, hollow microspheres with nanofilaments of $W_2O_3$ are used as sensor material for gas detection (Wang, G., Ji, Y., et al., 2006, J Phys Chem. B, vol. 110, no. 47, p. 23777) or as catalyst when used together with $SiO_2$ (Van Schalkwyk, C., Spamer, A., et al., 2003, Applied catalysis. A, vol. 255, no. 2, p. 121). Hollow microspheres with nanofilaments of strontium titanate ($SrTiO_3$) find applications in varistors or are used in tunable HTS (high temperature superconducting) microwave filters. Like $TiO_2$, $\alpha$-$Fe_2O_3$ is used for the nanofilaments of the hollow microspheres of the present invention for water treatment.

In an article of Sigmund, W., Yuh, J., et al. (2006, J. Am. Ceram. Soc., vol. 89, no. 2, p. 395) nanofibers made of $NiFe_2O_4$, $Fe_3O_4$, $Pb(Zr_{0.52}Ti_{0.48})O_3$, $MgTiO_3$, $NiTiO_3$, $Al_2O_3$—$B_2O_3$, $CeO_2$, $ZrO_2$, $Al_2O_3$, $GeO_2$, $Mn_2O_3$—$Mn_3O_4$, $CO_3O_4$, $Nb_2O_5$, $TiO_2$, $NiO/ZnO$, $PVP$-$TiO_2$, $SnO_2$, $La_2CuO_4$, $SiO_2$ and $BaTiO_3$ are described which can be used for manufacturing hollow microspheres according to the present invention. In another example the article of Sigmund, W., Yuh, J., et al. (2006, supra) refers to nanofibers made of $SiO_2$ which is coated with AlN. Hollow microspheres of the present invention whose nanofilaments comprise such coated nanofibers can be used in space-based applications. Other materials described in the article of Sigmund, W., Yuh, J., et al. (2006, supra) are fibers made of ferroelectric materials like $BaTiO_3$ or $Pb(Zr, Ti)O_3$. Also described are magnetic nanofibers made of $NiFe_2O_4$ and $Fe_3O_4$ which can be used for the manufacture of hollow porous microspheres of the present invention. $La_2CuO_4$ for example is one of the potential materials for commercialization as nitrogen monoxide (NO) sensor.

A material of particular interest for nanofilaments is titanium dioxide ($TiO_2$). Titanium dioxide ($TiO_2$) is one of the most used photoactive and one of the most practical of the semiconductors for widespread applications such as water purification, wastewater treatment, hazardous waste control, air purification, solar cells, gas sensor, pigments, cosmetics and water disinfection. $TiO_2$ is known due to its physicochemical properties, e.g., high quantum efficiency, nontoxicity, low cost, chemical stability, etc. Various morphologies of one-dimensional (1D) nanosized $TiO_2$, e.g. nanowires, nanofibers and nanotubes, have been widely prepared by various physical and chemical methods (Liu, Z., Sun, D. D., et al., 2007, Nano Lett., vol. 7, p. 1081).

In general, $TiO_2$ has three major crystal structures: rutile, anatase and brookite. However, only rutile and anatase play the role in the $TiO_2$ photocatalysis. Anatase phase is a stable phase of $TiO_2$ at low temperature (about 400° C. to about 600° C.) and is an important crystalline phase of $TiO_2$. Rutile is a stable phase of $TiO_2$ at high temperature (about 600° C. to about 1000° C.). Thus, in one aspect of the present invention nanofilaments of $TiO_2$ are in the rutile and/or anatase phase.

It is one advantage of titanium dioxide when used as adsorbent for the removal of contaminants that it has a high regenerative potential. The spent titanium dioxide can be regenerated via photocatalytic oxidation (PCO) process (Fang, H., Sun, D. D., et al., 2005, Water Science & Technology, vol. 51, no. 6-7, p. 373-380). The PCO process has been reported as a possible alternative for removing organic matters from potable water. A redox environment will be created in a PCO process to mineralize organic matter and sterilize bacteria adsorbed on the surface of the photocatalyst into carbon dioxide and water when the semiconductor photocatalyst is illuminated by light source (usually UV light) in a PCO process.

Normally titanium dioxide powders are used as photocatalytic material for the cleaning of wastewater. Processes for cleaning wastewater often use a combination of $TiO_2$ and membrane filtration. The membrane comprises small pores for filtering wastewater in which $TiO_2$ particles are dissolved. Unfortunately, recycling and reuse of titanium dioxide powder is an existing problem, particularly separation of titanium dioxide powder from wastewater treated for example in a membrane reactor. Small $TiO_2$ particles of the $TiO_2$ powder used often clog the pores of the filtration membrane.

Moreover, titanium dioxide powder, such as P25 from Degussa, does not present individually in aqueous system, but rather as physically unstable complex of primary aggregates ranging from 25 nm to 0.1 μm. These physically unstable complex aggregates reduce the surface area/active sites and subsequently affect its photocatalytic activity (Qiao, s., Sun, D. D., et al., 2002, Water Science Technology, vol. 147, no. 1, p. 211-217).

Therefore, in one aspect of the present invention the at least one metal oxide or metal sulfide which is used for manufacturing nanofilaments is a photocatalytic material. In one example $TiO_2$ is used as photocatalytic material. Using hollow microspheres of the present invention made of a photocatalytic material, such as $TiO_2$ avoids the problems which one normally encounters when using, for example titanium dioxide powder, such as P25 as described in the previous paragraph. Due to their spherical shape and size surface damage of filtration membranes in a membrane reactor can be avoided. Hollow microspheres made of $TiO_2$ nanofilaments can also be used to avoid irreversible membrane fouling because they inhibit, for example, that small particles dissolved in wastewater clog the pores of filtration membranes which have in general a diameter of a few hundred nanometers up to 2 μm. $TiO_2$ microspheres of the present invention sit in front of the pores of the filtration membrane and avoid smaller particles to clog such pores. Due to their hollow and porous structure such $TiO_2$ microspheres still allow passage of water through the filtration membrane. As previously described, even though the hollow microspheres of the present invention are much larger than commonly used particles made of $TiO_2$, like P25, the BET surface is retained due to its porous hollow structure.

In another aspect the present invention refers to a method of manufacturing at least one hollow microsphere according to the present invention, wherein said method comprises:

spray drying a mixture of a surfactant and nanofilaments.

Use of a mixture of surfactant and nanofilaments allows for the first time to manufacture hollow porous microspheres whose circumferential wall is made of nanofilaments and not a layered more continuous circumferential wall as in Nagaoka, S., Hamasaki, Y. et al. (2002, supra), Li, X. Z. and Liu, H. (2003, supra) and Liu, Z., Sun, D. D. et al. (2007, supra). In addition the microspheres referred to in Nagaoka, S., Hamasaki, Y. et al. (2002, supra), Li, X. Z. and Liu, H. (2003, supra) have a solid core while the hollow microspheres referred to in Liu, Z., Sun, D. D. et al. (2007, supra) comprise a solid circumferential wall.

As described above any kind of material can be used for the manufacture of nanofilaments. Methods of manufacturing nanofilaments such as nanowires, nanofibers and nanotubes are known in the art. Nanowires, nanotubes and nanofibers can, for example, be manufactured by any method known in the art. Such methods include, but are not limited to hydrothermal reaction, electrospinning or a sol-gel method.

Manufacturing of nanowires and nanofibers using the hydrothermal method or hydrothermal synthesis is described, for example, by Hidalgo et al. (2007, Catalysis Today, vol.

129, p. 50-58) and Yuan, Z.-Y., Su, B.-L. (2004, Colloids and Surfaces A: Physicochem. Eng. Aspects, vol. 241, p. 173).

Figure 12A:
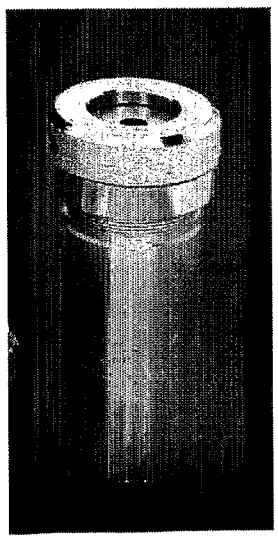
FIG. 12A shows an autoclave which can be used for the hydrothermal synthesis of nanowires or nanofibers.

An overview over hydrothermal method of crystallizing substances is provided by Chen, X. and Mao, S. S. (2006, J Nanosci Nanotechnol, vol. 6, no. 4, p. 906) or Mao, Y., Park, T. J., et al. (2007, Small, vol. 3, no. 7, p. 1122). In brief, the hydrothermal method includes various techniques of crystallizing materials from high-temperature aqueous solutions at high vapor pressures. The crystal growth is performed in an apparatus consisting of a steel pressure vessel called autoclave or bomb (see FIG. 12A) in which a nutrient (including the material which is supposed to crystallize) is supplied along with water or another solvent. A temperature gradient is maintained at the opposite ends of the vessel so that the hotter end dissolves the nutrient and the cooler end causes crystals to grow on the seeds provided in the vessel.

A large number of nanofilaments can been synthesized under hydrothermal conditions: elements, simple and complex oxides, tungstates, molybdates, carbonates, silicates, germanates etc. For example, the articles of Hidalgo et al. (2007, supra) and Kolen'ko, Y. V., Churagulov, B. R., et al. (2004, Appl. Cata. B: Environ., vol. 54, p. 51) describe the manufacture of nanostructured material made of titanium powder.

Factors influencing the diameter of nanofilaments during hydrothermal reaction include temperature, starting material and reaction time. For example, for the synthesis of nanowires with a length of about 20 nm to about 100 nm the temperature is between about 150° C. to about 200° C. Basic substances, such as sodium hydroxide can for example be used as starting material and oxides, such as $TiO_2$. The reaction time is about 2 to 3 days. In case the temperature is lower, for example, between about 120° C. to about 150° C., the nanofilament is likely to be a nanotube with a length between about 10 nm to about 15 nm. If the starting material is replaced with potassium hydroxide instead of sodium hydroxide, the product would be an ultrathin nanowire with a length between about 10 nm to about 15 nm.

Another method of manufacturing nanofilaments such as nanofibers and nanowires is electrospinning as described by McCann, J. T., Li, D. and Xia, Y., (2005, J. Mater. Chem., vol. 15, p. 735), Sigmund, W., Yuh, J., et al. (2006, supra), Bender, E. T., Katta, P., et al. (2006, Surf. Interface Anal., vol. 38, p. 1252), Madhugiri, S., Sun, B., et al. (2004, Microporous and Mesoporous Materials, vol. 69, p. 77) and Subbiah, T. and Bhat, G. S. et al. (2005, Journal of Applied Polymer Science, vol. 96, p. 557).

The formation of a thin fiber for a scaffold via 'electrospinning' is based on the uniaxial stretching (or elongation) of a viscoelastic jet derived from a polymer solution or melt. This technique is similar to the commercial processes for drawing microscale fibers except for the use of electrostatic repulsions between surface charges (rather than a mechanical or shear force) to continuously reduce the diameter of a viscoelastic jet or a glassy filament. Compared with mechanical drawing, electrostatic spinning is better suited for generating fibers with much thinner diameters, since the elongation can be accomplished via a contactless scheme through the application of an external electric field. Like mechanical drawing, electrospinning is also a continuous process and therefore should work well for high-volume production (Li, D. & Xia, Y. N., 2004, Advanced Materials, vol. 16, p. 1151-1170).

In electrospinning, a fiber is generated as the electrified jet (composed of a highly viscous polymer solution, see further below) is continuously stretched due to the electrostatic repulsions between the surface charges and the evaporation of solvent. As the fiber travels toward the surface of the collector (conductive plate), evaporation of the solvent in which the polymer or precursor material is dissolved occurs and the fiber is typically dry when arriving at the surface of the collector (conductive plate). To carry out this method, a syringe pump is used which squeezes a small amount of a complex fluid (precursor material and solvent) out of a needle which has a diameter of up to 100 μm. By varying the diameter of the opening of the needle the diameter of the nanofilament can be easily controlled. In one example a gauge needle is used. The metallic needle is attached to a high voltage source either positive or negative (producing a high voltage between about 1 to 50 kV). The droplet that forms at the end of the needle will change its form as soon as a voltage is applied. In addition to the surface tension and gravity force now additional forces shape a cone (the so called 'Taylor cone'). Depending on the experimental conditions the jet then starts to whip close to the collector that causes it to thin to a few hundred nanometers with lower limits in the tenths of nanometers.

The complex fluid containing the precursor material can consist of salt loaded polymer solutions, sol-gel systems, or nanoparticle slurries.

For example, precursor materials for the manufacture of nanofilaments of $TiO_2$ can be metallic alkoxides or organometallic precursors. Examples of titanium alkoxides can include, but are not limited to titanium methoxide, titanium ethoxide, titanium isopropoxide, titanium propoxide and titanium butoxide.

Such precursors can be supplemented with compositions which increase their viscosity to ensure that during electrospinning a fiber or wire is electrospun and not spherical nanoparticles. Such compositions which enhance the viscosity are known in the art of electrospinning. For example when $TiO_2$ is used polymer solutions such as polyvinylpyrrolidone (PVP) can be used to increase the viscosity.

Furthermore, the precursors can be treated to reduce the rate of hydrolysis, e.g., by ligand exchange. In case of $TiO_2$ acetic acid or acetylacetonate is used to reduce the rate of hydrolysis by ligand exchange of the acetate group with the alkyl group of the respective alkoxide.

Another method of manufacturing nanofilaments of the present invention, even though it is not used in the art as often as the hydrothermal method and electrospinning, is the sol-gel method. A "sol" is a dispersion of solid particles in a liquid where only the Brownian motions suspend the particles. A "gel" is a state where both liquid and solid are dispersed in each other, which presents a solid network containing liquid components. In general, the sol-gel method is based on the phase transformation of a sol obtained from metallic alkoxides or organometallic precursors. The sol, which is a solution containing particles in suspension, is polymerized at low temperature to form a wet gel. The wet gel is going to be densified through a thermal annealing to give an inorganic product like a glass, polycrystals or a dry gel. In general, the sol-gel process consists of hydrolysis and condensation reactions, which lead to the formation of the sol.

The sol-gel process can be performed according to any protocol. The nanofilaments, such as titanium oxide nanofilaments may be formed from an organometallic titanium precursor, for example in situ during the reaction process. Examples of such organometallic titanium precursors are titanium alkoxides which can include, but are not limited to titanium methoxide, titanium ethoxide, titanium isopropoxide, titanium propoxide and titanium butoxide.

For example in the article of Miao, Z., Xu, D., et al. (2002, NanoLetters, vol. 2, no. 7, p. 717) $TiO_2$ nanowires are manufactured using sol-gel method. An electrochemically induced sol-gel method is used to prepare TiO2 single-crystalline nanowire arrays. In this method a hydroxyl ion is generated due to the cathodic reduction and then the generation of OH⁻ ions increases the local pH at the electrode surface, resulting in a titanium oxyhydroxide gel formation in the pores of an anodic aluminium oxide (AAO) template. A final heat treatment results in an array of $TiO_2$ nanowires.

Cao, H. Q., Yu, Y., et al. (2001, Adv. Mater., vol. 13, p. 1393) describes for example the manufacture of CdS nanowires; Lakshmi, B. B., Patrisii, C. J., et al. (1997, Chem. Mater., vol. 9, p. 2544) describes the manufacture of $SiO_2$ nanowires, while Cheng, B. and Samulski, E. T. (2001, J. Mater. Chem., vol. 11, p. 2901) describe the manufacture of $In_2O_3$ nanowires.

Before spray drying the nanofilaments the nanofilaments are mixed with a surfactant to obtain a suspension for spray drying. According to the understanding of a person skilled in the art, the term "suspension" is considered to refer to a mixture of two substances wherein one substance is in the solid phase (in this case the nanofilaments) whiles the other one is in the liquid phase (surfactant (optionally plus an additional solvent)).

The nanofilaments can be dispersed in an organic or aqueous "solvent" before it is mixed with the surfactant. It is also possible that the nanofilaments and the surfactant are mixed at first and the solvent is added later. The choice of solvent depends on the kind of nanofilaments used. For example, some materials should not get into contact with water (for example $TiO_2$ nanofiber which is electrospun and has not yet been calcined). For such materials organic solvents such as ethanol, acetonitrile or acetone (to name only a few illustrative examples) are preferred. In other applications, e.g., water can be used as solvent (e.g. $TiO_2$ nanostructured material manufactured by hydrothermal treatment). A person skilled in the art will know what kind of solvent can be used for the different materials which are known in the art.

A "surfactant" as used herein is a member of the class of materials that, in small quantity, markedly affect the surface characteristics of a system; also known as surface-active agent. In a two-phase system, for example, liquid-liquid or solid-liquid, a surfactant tends to locate at the interface of the two phases, where it introduces a degree of continuity between the two different materials.

In general, surfactants are divided into four classes: amphoteric, with zwitterionic head groups; anionic, with negatively charged head groups; cationic, with positively charged head groups; and nonionic, with uncharged hydrophilic head groups. Each of them and mixtures of them can be used in the present invention. For the purposes of the present invention any kind of surfactant can be used as has been demonstrated in experiments described further below in the experimental section. It has been examined whether different kinds of surfactants have a different effect on the formation of hollow porous microspheres during spray drying. Therefore, three different kinds of surfactants have been examined. When comparing the effect of a nonionic surfactant, an anionic surfactant and a cationic surfactant on the formation of hollow porous microspheres now difference has been observed.

Illustrative examples of an anionic surfactant include, but are not limited to sodium dodecyl sulfate (SDS), sodium pentane sulfonate, dehydrocholic acid, glycolithocholic acid ethyl ester, ammonium lauryl sulfate and other alkyl sulfate salts, sodium laureth sulfate, alkyl benzene sulfonate, soaps, fatty acid salts or mixtures thereof.

Illustrative examples of a nonionic surfactants include, but are not limited to poloaxamers, alkyl poly(ethylene oxide), diethylene glycol monohexyl ether, copolymers of poly(ethylene oxide) and poly(propylene oxide), hexaethylene glycol monohexadecyl ether, alkyl polyglucosides (such as octyl glucoside, decyl maltoside), digitonin, ethylene glycol monodecyl ether, cocamide MEA, cocamide DEA, cocamide TEA, fatty alcohols (such as cetyl alcohol, oleyl alcohol) or mixtures thereof. In one illustrative example the nonionic poloaxamer used is F127.

Poloaxamers such as F127 are difunctional block copolymer surfactants terminating in primary hydroxyl groups. They are composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist having slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define it's physical form at room temperature (L=liquid, P=paste, F=flake (solid)) followed by two or three digits, the first digit(s) refer to the molecular mass of the polyoxypropylene core (determined from BASF's Pluronic grid) and the last digit×10 gives the percentage polyoxyethylene content (e.g., F127=Pluronic with a polyoxypropylene molecular mass of 4,000 g/mol and a 70% polyoxyethylene content). In the example given, poloxamer 407 (P407)=Pluronic F127.

Illustrative examples of cationic surfactant include, but are not limited to cetyl trimethylammonium bromide (CTAB), dodecylethyldimethylammonium bromide, cetylpyridinium chloride (CPC), polyethoxylated tallow amine (POEA), hexadecyltrimethylammonium p-toluenesulfonate, benzalkonium chloride (BAC), benzethonium chloride (BZT) or mixtures thereof.

Examples for amphoteric surfactants include, but are not limited to dodecyl betaine, sodium 2,3-dimercaptopropanesulfonate monohydrate, dodecyl dimethylamine oxide, cocamidopropyl betaine, 3-[N,N-dimethyl(3-palmitoylaminopropyl)ammonio]-propanesulfonate, coco ampho glycinate or mixtures thereof.

The concentration of the surfactant is between about 0.05 to 0.2 wt % based on the total weight of the resulting suspension. In another example the concentration of the surfactant is about 0.1 wt % based on the total weight of the resulting suspension The suspension of nanofilaments and surfactant comprises nanofilaments in a concentration between about 2 to 10 g/l. Higher concentrations of nanofilaments result in disappearance of the cavity inside the microsphere. In another example, the concentration is between about 4 g/l to 6 g/l or between about 4 g/l to 8 g/l.

Mixing of the surfactant and the nanofilaments can be achieved by using any method known in the art such as ultrasonic radiation; stirring of the nanofilaments and the surfactant using mechanical means, such as a magnetic stirrer; or rotating the flask in which the mixture is contained.

After obtaining the mixture of nanofilaments and surfactant, the mixture is to be spray dried to obtain the hollow microspheres of the present invention. Spray drying is a commonly used method of drying a liquid feed through a hot gas. The temperature of the gas depends on the amount and the kind of liquid content in the suspension that needs to be evaporated and can thus be readily determined by a person skilled in the art. In one example the temperature of the gas is between about 180° C. to about 190° C. while the pressure of compressed air is between about 70 kPa to about 140 kPa.

Figure 12B:
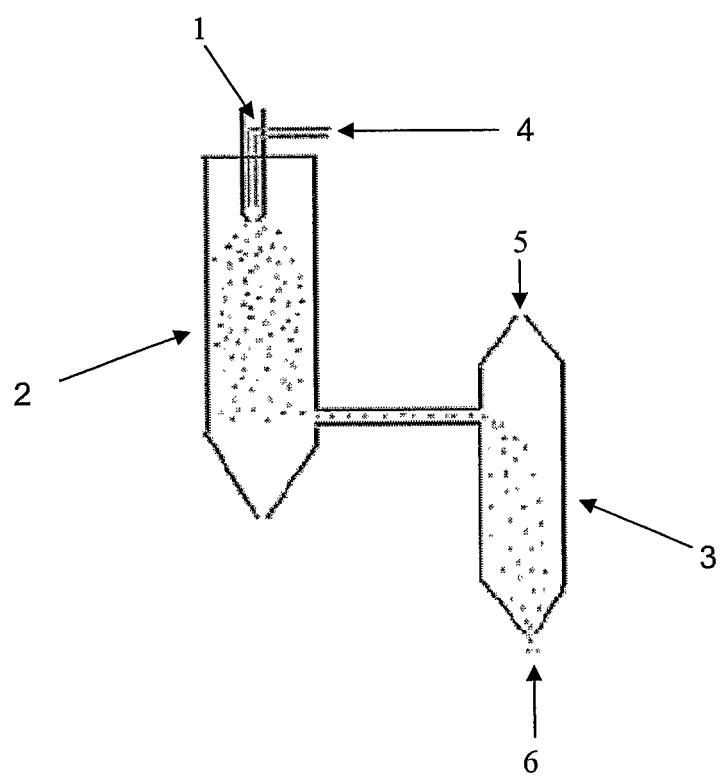
FIG. 12B shows a schematic diagram of the flow process of forming hollow microspheres of the present invention in a spray dryer. The suspension comprising the nanofilament and the surfactant is fed into the spray dryer via the feeding line 4 while the pressured hot air enters the evaporation tube 2 of the spray dryer via the inlet 1. After evaporation of the liquid in the suspension the microspheres formed are collected in the cyclone 3. While the hot air exits the cyclone 3 via the exhaust 5, the microspheres (indicated as grey dots in FIG. 12B) of the present invention exit the cyclone via the outlet 6.

The process that takes place during spray drying is illustrated in FIG. 8. The initial suspension droplet shrinks when the liquid content of it evaporates in the evaporation tube of the spray dryer. Once the entire liquid content of the suspension is evaporated the hollow microspheres of the present invention leave the spray dryer through the cyclone as illustrated in FIG. 12B.

In general, the hot gas is air but sensitive materials such as solvents like ethanol require oxygen-free drying and an inert gas, such as nitrogen gas, is used instead. Depending on the solvent used for obtaining the suspension of nanofilaments and surfactant air or an inert gas, such as nitrogen ($N_2$), is used. The suspension is pumped through an atomizer device that produces fine droplets which are dispensed or expelled through a nozzle into the evaporation tube of a spray dryer (see FIG. 12B). Atomizers vary with rotary, single fluid, and ultra-sonic designs.

For example, in rotary atomizers initial drops of suspension are gained by high speed rotary. Using rotary atomizers allows obtaining microspheres with a narrower size distribution. With single fluid atomizers only one kind of suspension or solution is sprayed from the atomizer.

The size of the hollow microspheres produced can be easily defined by adapting the size of the nozzle through which the suspension is atomized before being fed into the evaporation tube of the spray dryer. The nozzles diameter can be in the range of about 1 mm to about 500 mm. Small spray dryers have in general a nozzle diameter between about 1 mm to about 10 nm while larger spray dryer can have a nozzle diameter between about 10 mm and 500 mm. In one example, the diameter of the nozzle is about 7 mm.

Some microspheres might require a specific thermal treatment, for example to obtain a desired crystal structure or simply to remove any remaining liquid component, such as the surfactant. Therefore, the hollow microspheres can be subjected to a thermal treatment between about 30° C. or 50° C. to about 300° C. In case a thermal treatment is also used to obtain a certain crystal structure such a temperature treatment can be calcination. Therefore, in one aspect of the invention the method further comprises the step of drying and/or calcination of the hollow microspheres after spray drying.

In general, "calcination" means heating (a substance, in this case the hollow microspheres) to a high temperature (in general above 300° C.) but below the melting or fusing point, causing not only a loss of possibly remaining liquid (moisture) but also a reduction or oxidation, the decomposition of carbonates and other compounds, or a phase transition of the substance other than melting. In case metals are subjected to calcination, it includes the conversion of the metal into its oxides as a result of heating to a high temperature. The crystal phase of nanostructured material is also formed during calcination.

Calcination is usually carried out for several hours, for example 1, 2, 3, 4, 5, 6 hours or even more. Calcination is normally carried out in furnaces or reactors (sometimes referred to as kilns) of various designs including shaft furnaces, rotary kilns, multiple hearth furnaces, and fluidized bed reactors.

In general, calcination is carried out at a temperature between about 300° C. to about 700° C. or 400° C. to about 600° C. Calcination can also be carried out at a temperature of about 400° C., 500° C., 550° C. as well as at 600° C. These temperatures are only examples and a person skilled in the art will know that the temperature for calcination depends on the kind of material which has been used for manufacturing the hollow microspheres.

Different materials may require different temperatures for calcination. For example, when hollow microspheres made of $TiO_2$ are to be manufactured using the method of the present invention and the photocatalytic properties of $TiO_2$ are needed for the later application; the $TiO_2$ nanofilaments of the hollow microsphere should be in the rutile or anatase phase. As mentioned before, $TiO_2$ has three major crystal structures: rutile, anatase and brookite. However, only rutile and anatase play the role in the $TiO_2$ photocatalysis. Anatase phase is a stable phase of $TiO_2$ at low temperature (about 400° C. to about 600° C.) and is an important crystalline phase of $TiO_2$. Rutile is a stable phase of $TiO_2$ at high temperature (about 600° C. to about 1000° C.).

The ramp rate with which a hollow microsphere of the present invention is heated during calcination can, for example, be in the range of about 0.01° C./min up to about 5° C./min. A person skilled in the art will know that the ramp rate depends on the kind of material used for the nanofilaments. In general, a lower ramp rate results in better physical or chemical properties, like for example an improved crystal phase which can result in better photocatalytic activity in case photocatalytic materials, like $TiO_2$ are used. In case of $TiO_2$, the objective of calcination is to transfer amorphous $TiO_2$ into the anatase or rutile phase. A (s)lower ramp rate can form a more homogeneous crystal phase which results in higher photocatalytic activity. For example in one aspect a ramp rate of 2° C./min is used.

Figure 11:
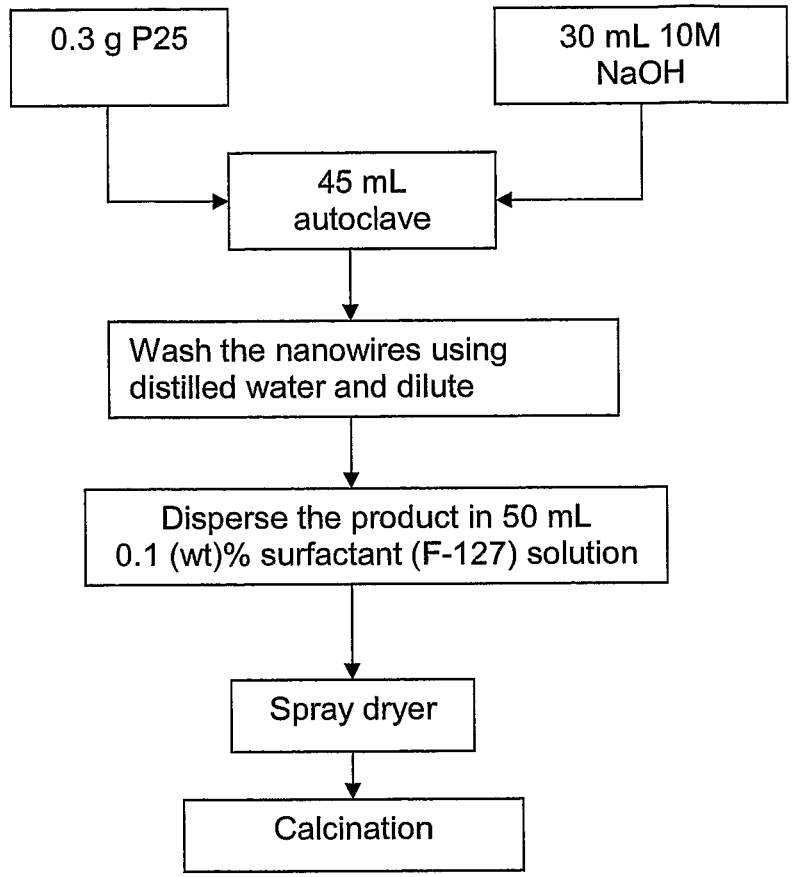
FIG. 11 shows a flowchart for a specific example of the present invention. This example illustrates a hydrothermal reaction-spraying-calcination process for fabrication of $TiO_2$ nanowire hollow microspheres which will be explained in more detail in the following detailed description of the invention.

FIG. 11 illustrates a specific example of how to obtain hollow microspheres according to the method of the present invention. In this illustrative example hollow microspheres have been manufactured whose nanofilaments are made of $TiO_2$.

In this example, $TiO_2$ nanowires are obtained by treating $TiO_2$ powders (such as P25 from Degussa or from Taixing Nano-Materials Company in China) within steel pressure vessels autoclave (see for example FIG. 12A) under controlled temperature and/or pressure in strong basic solution, such as NaOH. In this case 0.20 g of $TiO_2$ powder (P25, Degussa) (up to 1 g can be used) is mixed with 30 ml 10 M NaOH solution in 45 ml Teflon-lined autoclave container and is then subjected to a hydrothermal reaction.

It is well accepted that during hydrothermal reaction, some of the Ti—O—Ti bonds are broken and Ti—O—Na and Ti—OH bonds are formed, which results in the formation of $TiO_2$ nanowires (Yoshida, R., Suzuki, Y., Yoshikawa, S., 2005, supra; Chen, X., Mao, S. S., 2007, Chem. Rev., vol. 107, p. 2891).

After the hydrothermal reaction in an furnace for 2 days at 180° C., a white pulp suspension consisting of nanowires can be collected which is washed with distilled water and diluted with hydrochloric acid solution (pH 2) for 3 times ($HNO_3$ can also be used). Subsequently 0.1 wt.-% surfactant (F-127) is added into the nanowire suspension before subjecting it to spray drying.

In general, for spray drying the blow rate used can be between about 0.5 $m^3$/min to about 1.1 $m^3$/min. The feed flow rate can be between about 4 ml/min to about 16 ml/min. The gas temperature at the inlet of the spray dryer can be between about 120° C. to about 195° C. and the pressure at the inlet of the spray dryer can be between about 7 kPa to 14 kPa. Those values can change depending of the spray dryer model used for manufacturing the hollow porous microspheres of the present invention.

In the example illustrated in FIG. 11, spray drying is carried out with compressed air at a pressure of about 10 kPa and the gas for drying is heated to about 190° C. The blower flow rate is about 0.7 m³/min while the feed flow rate is about 8 ml/min. After spray drying the hollow $TiO_2$ microspheres obtained have been calcined at about 600° C. to obtain $TiO_2$ in the anatase phase.

Due to the photocatalytic properties of photocatalytic materials, such as $TiO_2$ the invention is directed in one aspect to a method of cleaning contaminated water comprising filtering the contaminated water through a compartment comprising hollow microspheres of the present invention or hollow microspheres obtained according to the method of the present invention wherein the hollow microspheres obtained by the method are made of a photocatalytic material, such as $TiO_2$.

The present invention also refers to the use of hollow microspheres of the present invention or hollow microspheres obtained by a method of the present invention as catalyst, or chromatographic material, or light-weight structural material, or thermal insulators, or acoustic insulators or electrical insulators or any of the other applications mentioned further above. In one example, the present invention refers to the use of catalysts comprising the hollow microspheres for cleaning contaminated water or hydrogen production or cracking oil or energy production or the manufacture of solar cells.

The term "contaminated water" refers to "wastewater" "raw water" or "sewage" which includes municipal, agricultural, industrial and other kinds of contaminated water. In general, any kind of contaminated water can be treated using the hollow microspheres obtained by the method of the present invention. In one example, the contaminated water has a total organic carbon content (TOC) of about 20 mg/l.

By "consisting of" is meant including, and limited to, whatever follows the phrase "consisting of". Thus, the phrase "consisting" of indicates that the listed elements are required or mandatory, and that no other elements may be present.

By "comprising" it is meant including, but not limited to, whatever follows the word "comprising". Thus, use of the term "comprising" indicates that the listed elements are required or mandatory, but that other elements are optional and may or may not be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Fabrication of $TiO_2$ Nanowire Microspheres

As previously mentioned, fabrication of nanowire is known in the art (Yuan, Z.-Y., Su, B.-L., et al., 2004, Colloids Surf. A, vol. 241, p. 173; Du, G. H., Chen, Q., et al., 2003, Phys. Rev. B, vol. 67, 035323). In one example described herein, $TiO_2$ powder (Degussa, P25) has been mixed with 10 M NaOH solution in a Teflon-lined autoclave container and placed in the oven at 180° C. for 2 days to undergo a hydrothermal reaction. The white pulp-like product in the autoclave has been washed with 0.1 M HCl, with the assistance of ultrasound. Subsequently, pH has been neutralized by repeated washing with deionized water. Unless otherwise stated, the as-synthesized nanowire powders have been added into 0.1 (wt) % surfactant (Pluronic F127) aqueous solutions to obtain 8 g/l $TiO_2$ suspension feed for spray-drying. Then, the suspension has been sprayed using a spray dryer (EYELA SD-1000) to produce the primary nanowire microspheres. The temperature of the gas for drying of the $TiO_2$ suspension which is expelled into the evaporation tube of the spray dryer is 190° C. The pressure with which the $TiO_2$ suspension is dispensed into the evaporation tube is about 10 kPa. The blower flow rate is about 0.7 m³/min while the feed flow rate is about 8 ml/min. After collecting the hollow $TiO_2$ microspheres exiting the spray dryer through the cyclone, the nanowire microspheres have been calcined at 600° C. for 2 h with a heating ramp of 2° C./min to obtain final $TiO_2$ nanowire microspheres.

Characterization of the $TiO_2$ Nanowire Microspheres

A JEOL 6340 field emission scanning electron microscopy (FESEM) and a JEOL 2010 transmission electron microscopy (TEM) have been used to observe the morphologies of the $TiO_2$ nanowire microspheres. The crystal structures and the phase compositions of samples have been identified using a Bruker AXS D8 Advance X-ray diffractometer with monochromated high-intensity Cu Kα irradiation ($\lambda$=1.5406 Å) at a scanning rate of 2°/min. The $N_2$ adsorption-desorption isotherms have been obtained at liquid nitrogen temperature (77 K) using a Quantachrome Autosorb 1 instrument. Before the measurement, the samples have been outgassed under vacuum for 5 h at 150° C. Specific surface areas have been calculated by the Brunaur-Emmett-Teller (BET) method using the adsorption data at the range from $P/P_0$=0.05 to 0.35 just below the capillary condensation, and the pore diameter distribution curve has been derived from the adsorption branch by the BJH method. A thermalgravimeter analyzer (TGA) has been used to monitor the degradation of surfactant in the sample. Measurements have been taken with a heating rate of 5° C./min from 30 to 700° C.

Evaluation of the Photocatalytic Activities of $TiO_2$ Nanowire Microspheres

Methylene blue (MB) has been used as the model chemical to investigate the photocatalytic activity of the $TiO_2$ nanowire microspheres. An Upland 3SC9 Pen-ray lamp (254 nm) has been immersed into solution to provide UV light. Air has been pumped into the solution to provide mixing for the catalyst and solution, as well as to induce oxygen into the system for oxidation. The aqueous system containing methylene blue (MB) (20 mg/L, 500 mL) and $TiO_2$ nanowire microspheres (0.5 g/L) has been mixed in the dark for 30 min to reach the adsorption equilibrium of methylene blue (MB) with the photocatalyst, before the UV lamp has been switched on. Commercial $TiO_2$ (Degussa P25) has been adopted as the reference for comparison. The characteristic absorption at $\lambda=670$ nm has been chosen to monitor the concentration of MB during the photodegradation process. TOC (total organic carbon) has been measured using a Shimadzu TOC-5000 analyzer.

Results of Experiments

The as-synthesized and calcined samples have been examined by FESEM, and the images at different magnification are shown in FIG. 1. From the low magnification image (FIG. 1a) of the as-synthesized sample, it has been found that microspheres, having 3-10 μm in diameter, have been produced in copious amounts. After calcination at 600° C., it can be observed that the spherical structure of the photocatalysts retained and with no apparent decrease in microspherical size (FIG. 1c). A typical FESEM image of a single as-synthesized microsphere is presented in FIG. 1b, in which it can be easily seen that these microspheres have been made of nanowires and surfactants. After calcination the surfactants have been completely removed and a porous structure has been left behind on the microspheres (FIG. 1d). A close up view of the nanofibers can be seen in FIG. 1B.

Figure 2:
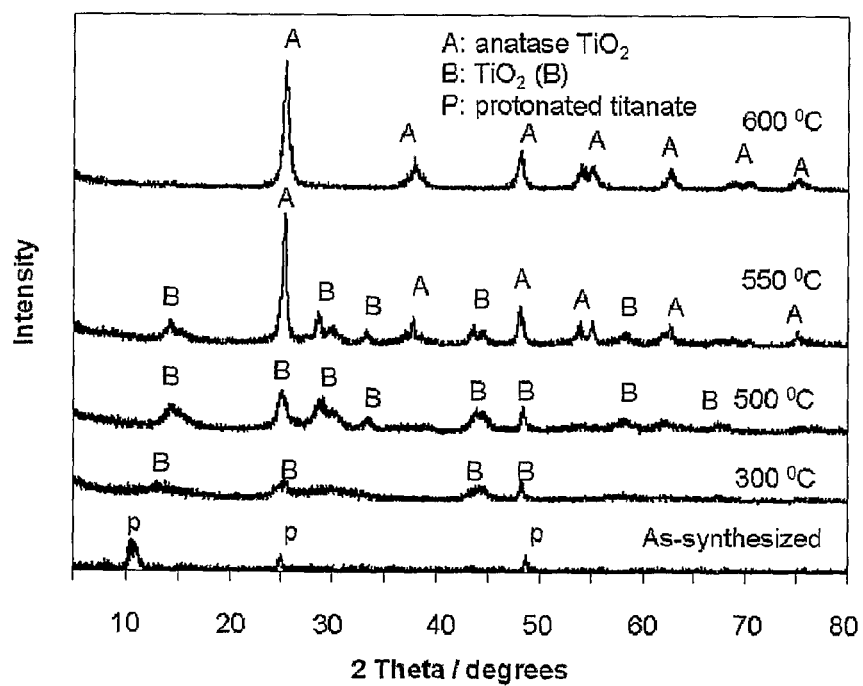
FIG. 2 shows XRD patterns of hollow $TiO_2$ microspheres calcined at different temperatures. As can be seen from FIG. 2, with increasing temperature (300 to 600° C.) the crystal phase of titanium oxide is shifting more to its photocatalytic more active anatase phase (A).

The crystal structures and the phase compositions of the nanowire microspheres calcined at different temperatures have been identified by wide-angle XRD as shown in FIG. 2. The diffraction pattern of the as-synthesized nanowires is similar to that expected for protonated titanate ($H_2Ti_2O_5$) with lepidocrocite-related layered structure (JCPDS 47-0124). No additional peaks of other impurities including starting P25 $TiO_2$ and NaCl have detected. These results are consistent with the results of other researchers (Zhang, H., Li, G. R., 2007, J. Phys. Chem. C, vol. 111, p. 6143; Pavasupree, S., Suzuki, Y., 2005, J. Solid State Chem., vol. 178, p. 3110). Upon calcination at 300° C., some XRD peaks for protonated titanate have become weaker or disappeared, while some new diffraction peaks of monoclinic $TiO_2$ (B), (JCPDS 35-0088) appeared. The dehydration of protonated titanate and the phase transition process have been accelerated by sintering the samples at higher temperatures. Upon calcination at 500° C., the XRD peaks of protonated titanate completely disappeared and the resulting XRD peak positions match well with the diffraction of the monoclinic $TiO_2$ (B), indicating that the protonated titanates have been fully dehydrated and converted into $TiO_2$ (B). Further increase in calcination temperatures would result in phase transformation from $TiO_2$ (B) to anatase. Upon calcination at 550° C., anatase phase was found to coexist with $TiO_2$ (B). The pure anatase phase (JCPDS 21-1272) has been achieved when the sample has been calcined at 600° C.

Figure 3:
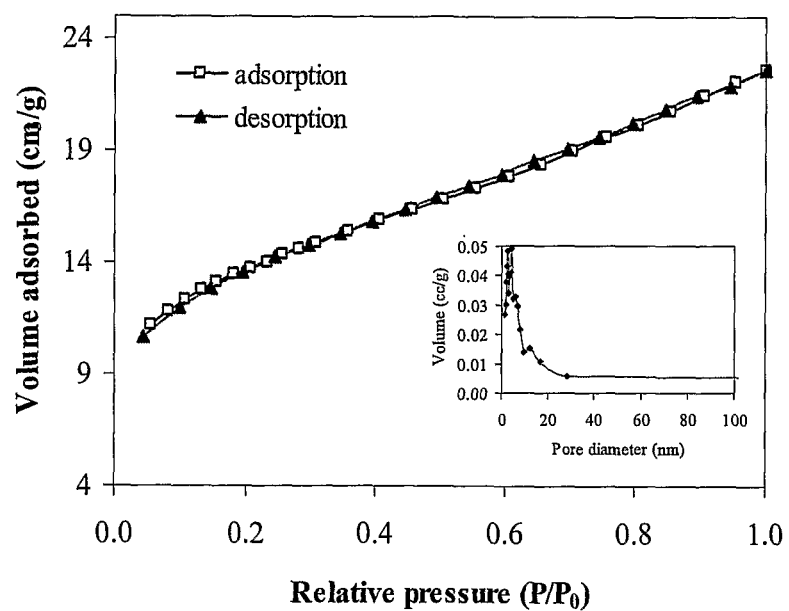
FIG. 3 shows the nitrogen adsorption and desorption isotherms and pore size distribution curve (inset) of $TiO_2$ nanowire hollow microspheres. Based on FIG. 3 the surface area as well as its pore-size distribution has been determined. BET surface area of the calcined $TiO_2$ nanowire microsphere has been revealed to be 38.2 $m^2/g$, which is very close to that of $TiO_2$ nanowire powder.

Nature of the texture of $TiO_2$ nanowire microspheres has been further determined by measurement of its surface area, as well as its pore-size distribution, which has been obtained by the nitrogen adsorption-desorption isotherm as shown in FIG. 3. BET surface area of the calcined $TiO_2$ nanowire microsphere has been revealed to be 38.2 $m^2g^{-1}$, which is very close to that of $TiO_2$ nanowire powder samples obtained without spray drying (39.6 $m^2g^{-1}$). As shown in FIG. 1A(b), the interlaced nanowires constitute the wall of microspheres and create the micropores with pore size ranging from 50-150 nm. Moreover, the insert of FIG. 3 shows the pore-size distribution plot of $TiO_2$ nanowire microspheres exhibiting a mean pore diameter of 5 nm. Thus, the multi-scale macro/meso-porosity of the resulting $TiO_2$ nanowire microspheres is high enough to prevent the decrease in surface area even after aggregation due to the spray drying process. This greatly benefits the photocatalytic activity of the micro spheres.

Figure 4:
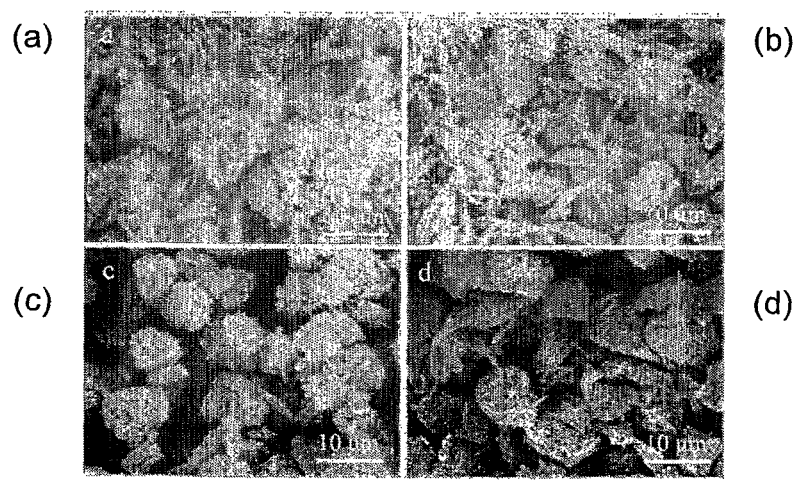
FIG. 4 shows FESEM images of the $TiO_2$ hollow microspheres fabricated using different concentration of surfactant solution. (a) 0 wt %, (b) 0.01 wt %, (c) 0.05 wt % and (d) 0.2 wt %. The observations from FIG. 4 allow the conclusion that the presence of a surfactant is critical to the formation of nanowire microsphere. Scale bar FIG. 4 (*a*) to (*d*): 10 µm.

A systematic study was carried out to investigate the formation mechanisms of the $TiO_2$ nanowire microspheres. Firstly, the role of F127 on the formation of $TiO_2$ nanowire microspheres has been studied by varying its concentration in the nanowire feed suspension prepared for spray-drying. Four different concentrations 0, 0.01, 0.05 and 0.2 wt % F127 solutions have been used to prepare the nanowire suspension, and the FESEM images of their products are shown in FIG. 4a-d respectively. The 0 wt % F127 (deionized water) results show that few microspheres have been fabricated (FIG. 4a). After increasing the F127 concentration to 0.01 wt %, more microspheres appeared as shown in FIG. 4b. When the F127 concentration reached 0.05 wt %, few dispersed nanowires have been visible and most of the nanowires have been assembled as microspheres as shown in FIG. 4c. After increasing the F127 concentration to 0.1 wt %, the microspherical products have been more uniform as shown in FIG. 1a. Further increment of the F127 concentration to 0.2 wt % did not result in significant difference to the microspherical size and structure. However, when F127 concentration is greater than 0.3 wt %, the suspension is more viscous and more difficult to be dried and it is thus difficult to attain the required microspherical structure. The above observations concluded that the presence of a surfactant, such as F127 is critical to the formation of nanowire microsphere and a very suitable concentration of F127 to be added is at 0.1 wt %.

Figure 5:
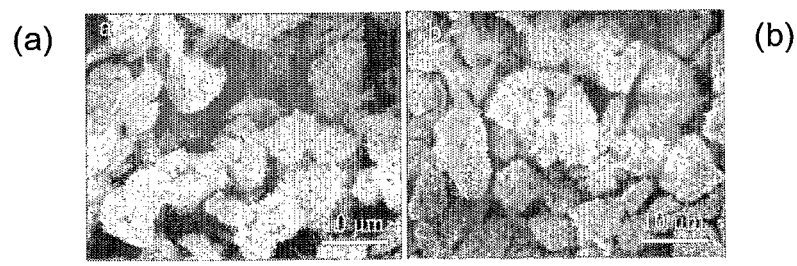
FIG. 5 shows FESEM images of the $TiO_2$ hollow microspheres using different surfactants. (a) 0.1 wt % anionic surfactant SDS and (b) 0.1 wt % cationic surfactant CPC. It can be concluded that the kind of surfactant used appears not to influence the formation of hollow microspheres. Scale bar FIG. 5(*a*) and (*b*): 10 µm.

F127 is a nonionic difunctional block copolymer surfactant terminating in primary hydroxyl groups. In order to investigate the effect of the ionic type of polymer on the fabrication of the aggregates, anionic surfactant sodium dodecyl sulphate (SDS) and cationic surfactant cetylpyridinium chloride (CPC) have been used, respectively. FIG. 5a-b show the FESEM images of the $TiO_2$ microspheres fabricated using 0.1 wt % SDS and CPC, respectively. As shown in FIG. 5, there is no apparent difference in the $TiO_2$ microspheres produced using SDS or CPC. These microspheres are also similar to those fabricated using F127. This indicates that there is no significant influence on the formation of nanowire microspheres due to differences in ionic types of surfactant.

Figure 6:
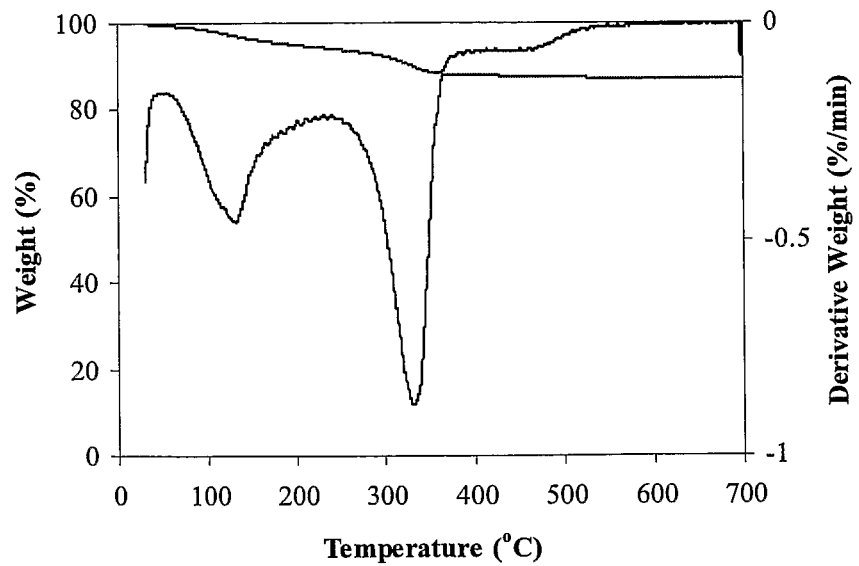
FIG. 6 shows the thermogravimetric analysis (TGA) curves for hollow microspheres.

As shown above, the presence of surfactant is important for the formation of microspheres. To investigate the change of surfactant during a hydrothermal treatment TGA has been used to monitor the weight change of nanowire microspheres with temperatures increment of 30° C. to 700° C. The initial weight ratio of F127 to nanowire in the suspension feed has been 1:9. As shown in FIG. 6, the surfactants have been mainly removed at two critical temperatures, namely, 140 and 330° C. Upon 350° C., all surfactant has been almost removed from the nanowire microspheres.

Figure 7:
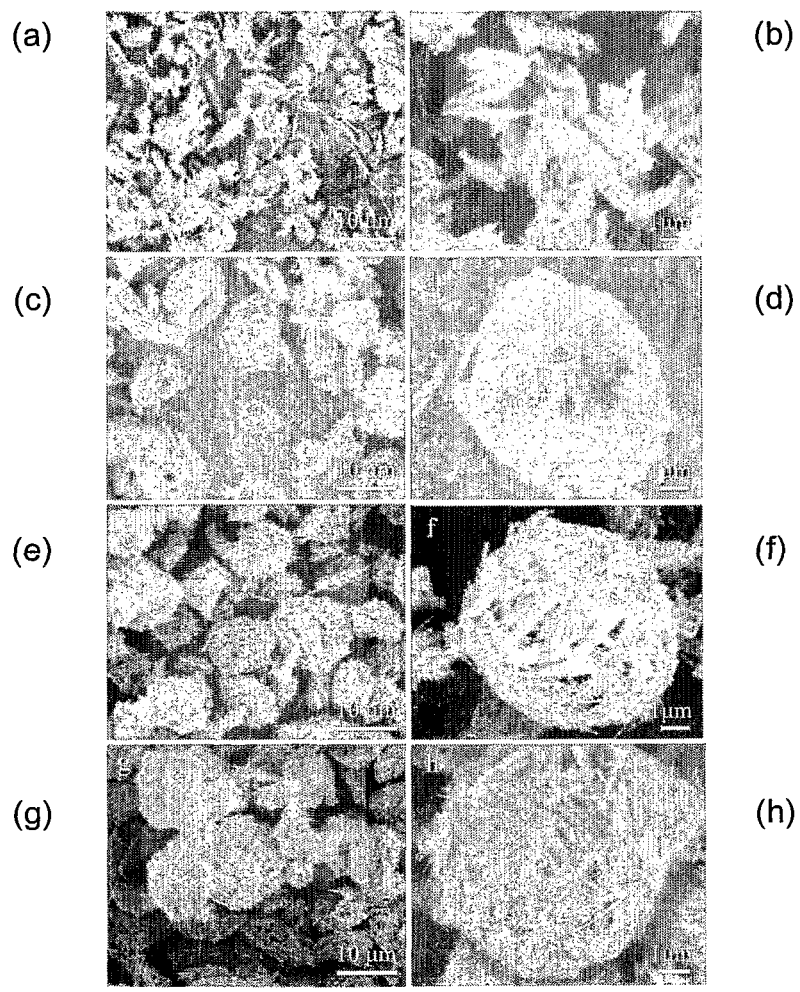
FIG. 7 shows FESEM images of hollow $TiO_2$ microspheres fabricated using different suspensions having different concentrations of nanofilaments.

In order to investigate the effect of varying nanowire concentration in the suspension feed on the formation of nanowire microspheres, four suspensions of different nanowire concentrations prepared using 0.1 wt % F127 have been used and the FESEM images of their products are shown in FIG. 7a-h. FIG. 7a shows the image of the products of 2 g/L nanowire suspension. It can be observed that the number of assemble nanowires is small. It is hypothesized that the nanowire concentration is still too low for the assembly of larger amounts of microspheres. As the nanowire concentration increased to 4 g/L, large amounts of microspheres have been visible in the products as shown in FIG. 7c. High magnification image (FIG. 7d) shows the microspheres are hollow and with an opening on the shell. The shell which consists of nanowires, has a porous morphology. At a nanowire concentration of 6 g/L, there has been a further increase in the quantities of microspheres in the products. However, the one central opening has been absent from the shell as shown in FIG. 7e. High magnification image (FIG. 7f) shows however that the porous morphology of the microsphere shell remained intact. Through the net pores between nanowires, the hollow structure is also clearly visible. At a nanowire concentration of 8 g/l, the microspheres became close-grained as shown in FIG. 1A(a) and (b). The pore size of the microspheres became smaller. Further increase in the concentration of nanowires to 10 g/L resulted in formation of more close-grained microspheres as shown in FIGS. 7g and h. The change in size of the microspheres is less apparent than the change in shape and structure. With the increase in nanowire concentration from between about 4 g/L to about 10 g/L, only a slight increase in microspherical size has been recorded.

According to the experimental results above, the possible mechanism of the formation of $TiO_2$ nanowire microspheres is shown in FIG. 8. In the absence of surfactant, the nanowires easily aggregate side by side because of their high specific surface energy. This may explain the absence of microspheres in the products of 0 wt. % F127. In the presence of surfactant, the nanowires are dispersed very well with ultrasonic assistance. The surfactant dissolves in water to form shells surrounding nanowires, preventing them from aggregating. The suspension feed of nanowires is pumped into the nozzle of the spray dryer and forced out of the orifice as a spray jet dispersion, which consists of droplets of nanowire suspension. As soon as the droplets come into contact with the drying air in the drying chamber, solvent evaporation takes place. Due to evaporation of water, the droplets shrink gradually and the concentrations of nanowire and surfactant in the droplets increase. With increasing concentration of surfactant, the droplets became more viscous. With the decrease in droplet diameter, the nanowires assemble towards the center of the droplet under surface tension. Nanowires then accumulate on the surface of the droplet, forming a microspherical shell. The structure of the nanowire microsphere is dependent on the nanowire concentration in the suspension feed for spray drying. If the nanowire concentration is very low (for example 2 g/L), the microspherical shell can not always form sufficiently due to insufficient nanowire content in the droplets when the solvent is completely evaporated, resulting that far less microspherical products is fabricated. At a low concentration (for example 4 g/L), the shell is formed leaving an opening to the hollow interior. At a high nanowire concentration, a shell will form before the solvent evaporates. Subsequently, after formation of the shell, the droplet continues shrinking as the solvent is being removed. The shell will be compressed further and more nanowires will accumulate on the shell, resulting in a thicker shell. Surfactant can be removed from the microspheres by subsequent calcination and crystallization resulted in less elastic nanowires, hence retaining the spherical shape of the end product.

Figure 9:
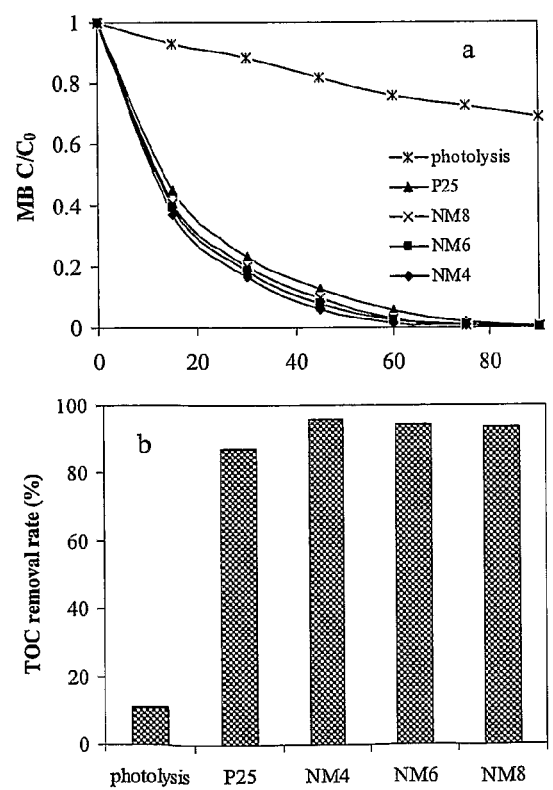
FIG. 9 illustrates changes in methylene blue (MB) concentration and total organic content (TOC) during the course of photolysis and photo catalytic degradation of MB in the presence of P25 and different hollow $TiO_2$ microspheres of the present invention. During photocatalytic degradation, MB is first decomposed into some small molecular fractions and then these small molecular fractions will be further degraded into carbon dioxide and water.

To demonstrate the photoactivity in degrading contaminants from water, three kinds of nanowire microspheres have been fabricated using 4 g/L, 6 g/L and 8 g/L nanowire suspension feeds. They are called NM4, NM6 and NM8, respectively, and have been used to investigate the photocatalytic degradation of methylene blue (MB). The changes in MB concentration during photocatalytic degradation are shown in FIG. 9. During photocatalytic degradation, MB is first decomposed into some small molecular fractions and then these small molecular fractions can be further degraded into carbon dioxide and water (Houasa, A., Lachheba, H., et al., 2006, Applied Catalysis B: Environmental, vol. 31, p. 145). For comparison purposes, UV irradiations without photocatalyst (photolysis) and with P25 have also been carried out. MB reduction in photolysis was less than 30% after an irradiation time of 90 min. The photocatalytic degradation of MB in $TiO_2$ nanowire hollow microspheres and P25 suspensions fitted the pseudo-first-order model. The apparent rate constants for the three kinds of nanowire microspheres NM4, NM6 and NM8 were 0.0639, 0.0632 and 0.0621 $min^{-1}$, respectively. These were better than that for P25 (0.0556 $min^{-1}$). In water, P25 $TiO_2$ nanoparticles coagulate easily to form submicron aggregates due to their high surface energy, and this results in the reduction of contact area with UV and organic reactants. The total organic content (TOC) results also showed similar results as shown in FIG. 9b. In the case of hollow $TiO_2$ nanowire microspheres of the present invention, the nanowires are assembled by "weaved" nanowires, forming macropores within the shell of hollow microspheres. These macroporous channels can serve as light-transfer paths, which means the macroporous structure of $TiO_2$ microspheres will allow UV light to penetrate its shell, so that the interior of microspheres can be effectively utilized as already suggested by Wang, X., Yu, J. C., et al. (2005, Langmuir, vol 21, p. 2552). This would also explain that no significant difference has been discovered among the photocatalytic activities of NM4, NM6 and NM8, although they possessed different shell wall thickness.

Figure 10:
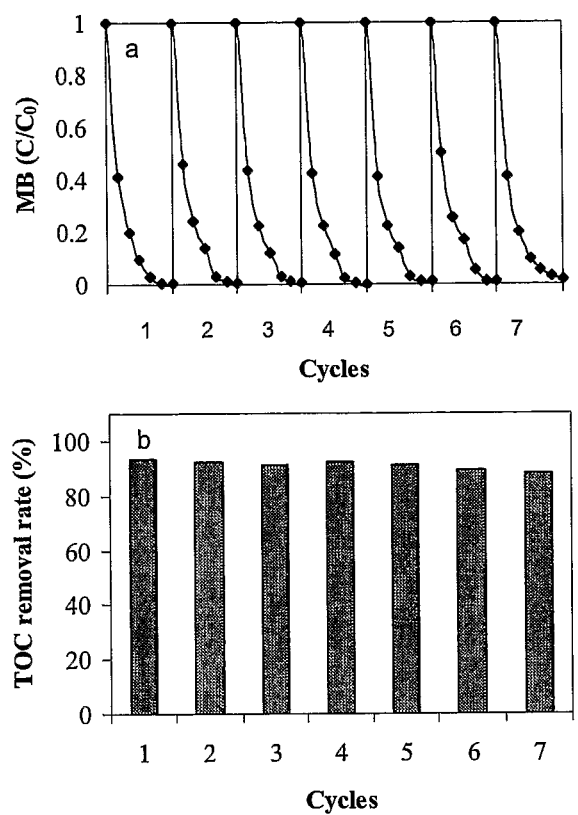
FIG. 10 shows the effect of repeated use of hollow $TiO_2$ microspheres of the present invention on its effectivity to remove organic matter from contaminated water.

The $TiO_2$ nanowire microspheres settle rapidly in the aqueous solution under gravity after stopping air bubbling, resulting in good separation of catalyst from the treated water. After 90 min of photocatalytic reaction, the respective photocatalysts have been recovered for SEM characterization. Micrographs showed collapse of some NM4 and NM6 nanowire microsphere, most probably due to a lower mechanical strength of their thin shell. However, NM8 retained their spherical shapes very well, with minimum collapse. To further investigate the stability of NM8 on photocatalytic activity and mechanical strength, NM8 have been repeatedly used in the MB photocatalytic degradation for 7 cycles. For each cycle, 90 min of irradiation has been applied and after the microspheres have settled by gravity, the supernatant has been dumped and refilled by new MB solution of the same concentration. After 7 cycles, very little broken nanowire microspheres have been found. The MB and TOC removal rates in every cycle are shown in FIG. 10. There has been no significant decrease in the MB removal rates. These results indicate that the NM8 exhibited stable photocatalytic activity and mechanical strength, which is pertinent in cost-effective engineering applications.

The invention claimed is:

1. A microsphere comprising a hollow space inside said microsphere; said microsphere consisting of a mesoporous and/or macroporous circumferential wall, wherein said circumferential wall is surrounding the entire hollow space of said microsphere; wherein the circumferential wall consists of nanofilaments, wherein the nanofilaments are comprised of a metal sulfide selected from the group consisting of CdS, $In_2S_3$ and ZnS; wherein said mesopores have a diameter between about 2 to about 50 nm and wherein said macropores have a diameter between about 50 to about 200 nm.

2. The hollow microsphere according to claim 1, having a diameter between about 1 μm to about 200 μm.

3. The hollow microsphere according to claim 1, wherein the nanofilaments are further comprised of a material selected from the group consisting of metal oxide, carbon, polymer and mixtures thereof.

4. The hollow microsphere according to claim 1, wherein said nanofilaments are aligned randomly.

5. The hollow microsphere according to claim 1, wherein said nanofilaments are selected from the group consisting of nanofibers, nanowires, nanotubes and mixtures thereof.

6. The hollow microsphere according to claim 1, wherein said microspheres have a diameter between about 2 to about 10 μm.

7. The hollow microsphere according to claim 1, wherein said nanofilaments have a diameter between about 10 to about 500 nm or between about 10 to about 200 nm or between about 20 to about 100 nm.

8. The hollow microsphere according to claim 3, wherein said at least one metal oxide or metal sulfide is a photocatalytic material or wherein said at least one metal oxide is the photocatalytic material $TiO_2$.

9. The hollow microsphere according to claim 3, wherein said metal oxide is selected from the group consisting of $TiO_2$, $SiO_2$, ZnO, $Fe_2O_3$, $W_2O_3$ $SrTiO_3$, $NiFe_2O_4$, $Fe_3O_4$, $Pb(Zr_{0.52}Ti_{0.48})O_3$, $MgTiO_3$, $NiTiO_3$, $Al_2O_3$-$B_2O_3$, $CeO_2$, $ZrO_2$, $Al_2O_3$, $GeO_2$, $Mn_2O_3$-$Mn_3O_4$, $Pb(Zr, Ti)O_3$, $Co_3O_4$, $Nb_2O_5$, NiO/ZnO, PVP-$TiO_2$, $SnO_2$, $La_2CuO_4$, $BaTiO_3$ and mixtures thereof.

10. The hollow microsphere according to claim 3, wherein said polymer is selected from the group consisting of 1,1,1, 3,3,3-hexafluoroisopropanol (HFIP), poly(urethanes), poly (siloxanes), poly(silicones), poly(ethylene), poly(vinyl pyrrolidone), polyaniline/polyethylene oxide blends, poly(2-hydroxy ethyl methacrylate), poly(N-vinyl pyrrolidone), poly(methyl methacrylate), poly(vinyl alcohol) (PVA), poly (acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), polyorthoesters and mixtures thereof or wherein said polymer is selected from the group consisting of collagen, poly(alpha esters), such as poly (lactate acid), poly(glycolic acid), polyorthoesters, polyanhydrides; cellulose ether, cellulose acetate, cellulose, cellulose ester, chitosan, gelatin, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde and copolymers or physical blends thereof.

11. The hollow microspheres according to claim 8, wherein said $TiO_2$ is in anatase and/or rutil phase.

12. A method of manufacturing at least one hollow microsphere, said microsphere comprising a hollow space inside said microsphere; said microsphere consisting of a mesoporous and/or macroporous circumferential wall, wherein said circumferential wall is surrounding the entire hollow space of said microsphere; wherein the circumferential wall consists of nanofilaments, wherein the nanofilammts are comprised of a metal sulfide selected from the group consisting of CdS, $In_2S_3$ and ZnS; wherein said mesopores have a diameter between about 2 to about 50 nm and wherein said macropores have a diameter between about 50 to about 200 nm, wherein said method comprises:
    spray drying a suspension of a surfactant and the nanofilaments; wherein said suspension comprises said nanofilaments in a concentration of between about 2 to 10 g/l.

13. The method according to claim 12, further comprising the step of drying and/or calcination after spray drying.

14. The method according to claim 12, wherein said suspension comprises said nanofilaments in a concentration between about 4 to 8 g/l.

15. The method according to claim 13, wherein said calcination is carried out at a temperature between about 300° C. to about 700° C.

16. The method according to claim 12, wherein the concentration of said surfactant is between about 0.05 to about 0.2 wt % based on the total weight of said resulting suspension or wherein the concentration of said surfactant is about 0.1 wt % based on the total weight of said resulting suspension.

17. The method according to claim 12, wherein said surfactant is selected from the group consisting of amphoteric surfactants, anionic surfactants, cationic surfactants, nonionic surfactants and mixtures thereof.

18. A method of cleaning contaminated water comprising filtering said contaminated water through a compartment comprising hollow microspheres, said microsphere comprising a hollow space inside said microsphere; said microsphere consisting of a mesoporous and/or macroporous circumferential wall, wherein said circumferential wall is surrounding the entire hollow space of said microsphere; wherein the circumferential wall consists of nanofilaments, wherein the nanofilaments are comprised of a metal sulfide selected from the group consisting of CdS, $In_2S_3$ and ZnS; wherein said mesopores have a diameter between about 2 to about 50 nm and wherein said macropores have a diameter between about 50 to about 200 nm.

19. A catalyst, or chromatographic material, or lightweight structural material, or thermal insulators, or acoustic insulators or electrical insulators comprising a hollow microsphere, said microsphere comprising a hollow space inside said microsphere; said microsphere consisting of a mesoporous and/or macroporous circumferential wall, wherein said circumferential wall is surrounding the entire hollow space of said microsphere; wherein the circumferential wall consists of nanofilaments, wherein the nanofilaments are comprised of a metal sulfide selected from the group consisting of CdS, $In_2S_3$ and ZnS; wherein said mesopores have a diameter between about 2 to about 50 nm and wherein said macropores have a diameter between about 50 to about 200 nm.

* * * * *